United States Patent
Boudjouk et al.

(10) Patent No.: US 6,482,912 B2
(45) Date of Patent: Nov. 19, 2002

(54) METHOD OF PREPARING AMINOFUNCTIONAL ALKOXY POLYSILOXANES

(75) Inventors: Philip Boudjouk, Fargo, ND (US); Thomas E. Ready, Page, ND (US); Bhanu P. S. Chauhan, Silver Spring, MD (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 09/771,921

(22) Filed: Jan. 29, 2001

(65) Prior Publication Data

US 2002/0156223 A1 Oct. 24, 2002

(51) Int. Cl.[7] .............................................. C08G 77/08
(52) U.S. Cl. ............................ 528/15; 528/31; 528/28; 528/29; 556/407; 556/425
(58) Field of Search ........................... 528/15, 31, 28, 528/29; 556/407, 425

(56) References Cited

U.S. PATENT DOCUMENTS

| | | | | |
|---|---|---|---|---|
| 4,059,581 A | * | 11/1977 | Prokai | 544/69 |
| 4,570,010 A | * | 2/1986 | Stuber et al. | 556/475 |
| 4,952,715 A | | 8/1990 | Blum et al. | 556/409 |
| 5,051,458 A | * | 9/1991 | Costanzi et al. | 524/99 |
| 5,128,494 A | | 7/1992 | Blum | 556/457 |
| 5,162,136 A | | 11/1992 | Blum et al. | 427/226 |
| 5,405,655 A | | 4/1995 | Blum et al. | 427/387 |
| 5,639,844 A | | 6/1997 | Blum et al. | 528/15 |
| 5,925,779 A | * | 7/1999 | Cray et al. | 556/425 |
| 6,258,968 B1 | * | 7/2001 | Eversheim et al. | 556/425 |

OTHER PUBLICATIONS

P. Boudjouk, et al., "Nickel Catalyzed Silane Reductions of α, β—Unsaturated Ketones and Nitriles," *Tetrahedron Letters* 39, pp. 3951–3952 (1998), Elsevier Science Ltd., Great Britain.

M. Chauhan, et al., "A New Catalyst for Exclusive β–Hydrosilylation of Acrylonitrile," *Tetrahedron Letters* 40, pp. 4127–4128 (1999), Elsevier Science Ltd., Great Britain.

L. Sommer, et al., "Group VIII Metal Catalyzed Reactions of Organosilicon Hydrides with Amines, Hydrogen Halides, and Hydrogen Sulfide," *J. Org. Chem.* 32, pp. 2470–2472 (1967), American Chemical Society, U.S.A.

R. Corriu, et al., "Selective Catalytic Route to Bifunctional Silanes. Catalysis by Rhodium and Ruthenium Complexes of the Alcoholysis of Diarylsilanes and the Hydrosilylation of Carbonyl Compounds," *J. Chem. Soc.; Chem. Comm.* 1, pp. 38–39 (1973), The Chemical Society, Great Britain.

B. Aylett, et al., "Silicon–Transition–metal Compounds. Part I. Silyltetracarbonylcobalt and Related Compounds," *J. Chem. Soc.*, pp. 1910–1916 (1969), Inorg. Phys. Theor., Great Britain.

B. Aylett, et al., "Silicon–Transition Metal Compounds. Part II. Preparation and Properties of Silylpentacarbonylmanganese," *J. Chem. Soc.*, pp. 1916–1920 (1969), Inorg. Phys. Theor., Great Britain.

B. Aylett, et al., "Silicon–Transition Metal Compounds. Part III. Reactions of Silytetracarbonylcobalt and Silypentacarbonylmanganese with Lewis Bases of Nitrogen and Phosphorous," *J. Chem. Soc.; Chem. Comm.*, pp. 1920–1924 (1969), Inorg. Phys. Theor., Great Britain.

B. Sternbach, et al., "The Preparation of Methoxysilanes by the Interaction of Monosilane and Methanol," *J. Amer. Chem. Soc.* 81, pp. 5109–5110 (1959), American Chemical Society, U.S.A.

B. Aylett, et al., "A Volatile Silicon–Transition–metal Compound," *J. Chem. Soc.; Chem. Comm.*, p. 217 (1965), The Chemical Society, Great Britain.

Y. Baay, et al., "Trimethyl– and Trichlorosilylcobalt Tetracarbonyls and the Hydrosilation of Ethylene," *Inorg. Chem.* 8 (4), pp. 986–994 (1969), American Chemical Society, U.S.A.

A. Chalk, "Group IV–Cobalt Complexes as Catalysis for Silylation and Cyclic Ether Polymerization," *J. Chem. Soc.; Chem. Comm.*, pp. 847–848 (1970), The Chemical Society, Great Britain.

P. Rakita, et al., "Reductive Solvolysis of Dimethylindenylsilane: Evidence for a Two–step Mechanism," *J. Chem. Soc.; Chem. Comm.*, pp. 533–534 (1973), The Chemical Society, Great Britain.

P. Reddy, et al., "Palladium–Catalyzed Dehydrogenative Polymerization between Hydrosilanes and Quinones of Hydroquinone," *Chemistry Letters*, pp. 250–251 (2000), The Chemical Society of Japan, Japan.

Y. Baay, et al., "Synthesis And Properties Of Trimethylsiyl Cobalt Tetracarbonyl And Related Compounds," *Inorg. Nucl. Chem. Letters* 3, pp. 159–161 (1967), Pergamon Press Ltd., Great Britain.

R. Corriu, et al., "Alcoolyse Selective D'Organosilanes Catalysees Par Un Complexe Du Rhodium," *J. Organomet. Chem.* 114, pp. 135–144 (1976), Elsevier Science S.A., The Netherlands.

R. Corriu, et al., "Reactions D'Organosilanes Catalyses Par Des Complexes Du Rhodium; Synthese D'Organosilanes Polyfonctionnels," *J. Organomet. Chem.* 127, pp. 7–17 (1977), Elsevier Science S.A., The Netherlands.

(List continued on next page.)

Primary Examiner—Margaret G. Moore
(74) Attorney, Agent, or Firm—Foley & Lardner; Charles G. Carter; Jason E. Pauls

(57) ABSTRACT

A method of preparing a aminofunctional alkoxy polysiloxane is disclosed. The method includes reacting a polyhydrosiloxane with an alcohol reactant containing an aminoalcohol to form the aminofunctional alkoxy polysiloxane. Linear and cyclic aminofunctional alkoxy polysiloxane are also disclosed. A coating composition comprising an aminofunctional alkoxy polysiloxane is also provided.

63 Claims, No Drawings

OTHER PUBLICATIONS

H. Ito, et al., "Highly stereoselective metathesis reaction between optically active hdyrosilane and copper(I) salt in 1,3–dimethyl-2–imidazolidinone," *J. Organomet. Chem.* 574, pp. 102–106 (1999), Elsevier Science S.A., The Netherlands.

J. Wang, et al., "Dehydrocoupling reactions of amines with silanes catalyzed by $[Et_2N)_3U][BPh_4]$," *J. Organomet. Chem.* 610, pp. 49–57 (2000), Elsevier Science S.A., The Netherlands.

Y. Li, et al., "Efficient Synthesis of Poly(silyl ether)s by Pd/C and $RhCl(PPh_3)_3$–Catalyzed Cross–Dehydrocoupling Polymerization of Bis(hydrosilane)s with Diols," *Macromolecules* 32, pp. 6871–6873 (1999), American Chemical Society, U.S.A.

R. Zhang, "Dehydrocoupling Polymerization of Bis–silanes and Disilanols to Poly(silphenylenesiloxane) As Catalyzed by Rhodium Complexes," *Macromolecules* 33, pp. 3508–3510 (2000), American Chemical Society, U.S.A.

Y. Blum, et al., "Modifications of hydrosiloxane polymers for coating applications," *Surface Coatings International Part B: Coatings Transactions 84 (1)*, pp. 27–33 (2001), OCCA, U.S.A.

M. Chauhan, et al., "An Efficient Pd–Catalyzed Route to Silyl Esters," *Organic Letters.* 2 (8), pp. 1027–1029 (2000), American Chemical Society, U.S.A.

A. Arruda, et al., "New organosilicon polymer for the extraction and luminescence analysis of uranyl in environmental samples," *Anal. Chim. Acta* 396, pp. 263–272 (1999), Elsevier Sience B.V., The Netherlands.

B. Chauhan, et al., "Dehydrogenative condensation of SiH and SH bonds. A metal–catalyzed protocol to stable thiopolysiloxanes," *Tetrahedron Letters* 41, pp. 1127–1130 (2000), Elsevier Science Ltd., The Netherlands.

Q. Fan, et al., "Synthesis and Properties of Polyurethane Modified with Aminoethylaminopropyl Poly(dimethyl siloxane)," *J. App. Polymer Sci.* 74, pp. 2552–2558 (1999), John Wiley & Sons, Inc., U.S.A.

B. Chauhan, et al., "New Neutral Carrier–type Ion Sensors. Crown Ether Derivatives of Poly(methylhydrosiloxane)," *Tetrahedron Letters* 40, pp. 4123–4126 (1999), Elsevier Science Ltd., The Netherlands.

Y. Cai, et al., "Surface properties of silicone–containing block–graft copolymer/polystyrene systems," *J. Adhesion Sci. Technol.* 13 (9), pp. 1017–1027 (1999), VSP, U.S.A.

B. Chauhan, et al., "A Catalytic Route to Grafted Silicones," *Organometallics* 20, pp. 2725–2729 (2001), American Chemical Society, U.S.A.

L. Lestel, et al., "Crosslinking of polyether networks by hydrosilylation and related side reactions," *Polymer* 31, pp. 1154–1158 (1990), Butterworth–Heinemann Ltd., Great Britain.

S. Yun, et al., "Synthesis and Ionic Conductivity of Supramolecular Layered Silicate Hybrids of Phosphotungstates and Poly(ethylene glycol) Dicarboxylates," *Chemistry of Materials* 11 (7), pp. 1644–1647 (1999), American Chemical Society, U.S.A.

T. Ready, et al., "Functionalized Polysiloxanes as Primer Components in Coating Systems," Power Point Slides from Presentation and Abstracts of Presentations, $32^{nd}$ Great Lakes 2000 Regional Meeting, American Chemical Society, 28 pp. (2000), Fargo, North Dakota, U.S.A.

T. Ready, et al., "New High Performance Polysiloxane Primers for Aluminum," Abstract and Power Point Slides from Presentation to Air Force Office of Scientific Research, 2000 AFOSR Corrosion Review, 26 pp. (2000), Duck Key, Florida, U.S.A.

C. Howie, et al., "Proton Inventory of the Transition State for Hydride Expulsion from Silicon," *J. Amer. Chem. Soc.* 95 (16), pp. 5286–5288 (1973), American Chemical Society, Book and Journals Division, U.S.A.

P. Boudjouk, et al., "Hydrosilylation Catalysed by Activated Nickel," *J. Chem. Soc.; Chem. Comm.*, pp. 1424–1425 (1991), The Chemical Society, Great Britain.

* cited by examiner

METHOD OF PREPARING AMINOFUNCTIONAL ALKOXY POLYSILOXANES

Statement Regarding Federally Sponsored Research or Development

The U.S. Government has a paid-up license in the present invention and the right (in limited circumstances) to require the patent owner to license others on reasonable terms as provided for by the terms of Grant Nos. F49620-96-1-0360 and F49620/99-0283 awarded by the Air Force Office of Scientific Research and Grant No. 9874802 awarded by the National Science Foundation.

BACKGROUND

Synthetic routes to functionalized polysiloxanes often suffer from complex methodologies, low yields, side reactions (e.g. involving rearrangements and/or degradation), or minimal characterization of the product(s). It generally known to synthesize alkoxysilanes under mild and neutral reaction conditions using metal-catalyzed oxidation reactions of monomeric hydrosilanes. The reported methods can suffer from the disadvantage of the non-selective modification of Si—H bonds, which leads to susceptibility of the Si—H bonds toward side reactions including dehydrocoupling, rearrangement and/or backbone degradation reactions. The formation of mixtures of α and β-isomers, insoluble materials and rearrangement products are common drawbacks of reported methods.

Accordingly, it would be advantageous to provide a method of preparing a poly((aminofunctional alkoxy)-alkylsiloxane) using a relatively simple method under relatively mild reaction conditions. It would also be advantageous to provide a method of preparing a poly ((aminofunctional alkoxy)-alkylsiloxane) that allowed for the selective alcoholysis of Si—H bonds without significant degradation of the siloxane backbone. It would also be advantageous to provide a method of preparing a poly ((aminofunctional alkoxy)-alkylsiloxane) that allowed for monitoring of the reaction progress (e.g. by NMR). It would also be advantageous to provide a poly((aminofunctional alkoxy)-alkylsiloxane) product in a relatively high yield. It would be desirable to provide a method of preparing a poly((aminofunctional alkoxy)-alkylsiloxane) having one or more of these or other advantageous features.

SUMMARY

The present invention relates to a method of preparing aminofunctional polysiloxanes. More particularly, the present invention relates to a method of preparing aminofunctional alkoxy polysiloxanes. The method includes reacting a polyhydrosiloxane with an alcohol reactant including an aminoalcohol to form the aminofunctional alkoxy polysiloxane. The reaction is typically carried out in the presence of a catalyst, e.g., a dehydrogenative coupling catalyst which includes a rhodium compound.

The present application also provides a coating composition which includes an aminofunctional alkoxy polysiloxane. The coating composition is particularly suitable as an adhesive or primer for coupling a topcoat to a substrate. The aminofunctional alkoxy polysiloxane may serve as the primary resin in the coating composition or in other embodiments, an aminofunctional alkoxy polysiloxane may act as a crosslinking agent and/or curing accelerator, e.g., in epoxy-based coating compositions.

The present aminofunctional alkoxy polysiloxane compound can be a linear and/or cyclic alkoxy polysiloxane. As used herein, the term "aminofunctional alkoxy polysiloxane compound" refers to an alkoxy substituted polysiloxane compound which includes one or more aminofunctional alkoxy groups. For the purposes of this application, the term aminofunctional alkoxy group refers to groups which include at least one basic nitrogen atom and encompasses groups resulting from the removal of a hydroxyl hydrogen atom from an amino functional alkanol (e.g., —O—CH$_2$CH$_2$—O—CH$_2$CH$_2$NH$_2$), an amino functional cycloalkanol, and/or an amino functional hydroxy-substituted aryl compound (e.g., —O—C$_6$H$_4$—O—CH$_2$CH$_2$NH$_2$). As employed herein, the term "aryl" refers to both hydrocarbon aromatic groups and heteroatom-containing aromatic groups. For example, the aminofunctional alkoxy group may be an aminofunctional pyridyloxy group (i.e., a group resulting from the removal of the hydroxyl hydrogen atom from an aminofunctional hydroxypyridine).

Amino groups are organic functional groups which contain a basic nitrogen atom. Examples of amino groups include aliphatic amino groups, such as mono-, di- and trialkylamino groups; cycloaliphatic amino groups, such a piperidinyl and piperazinyl groups; aromatic amino groups (i.e., where the basic nitrogen atom is part of an aromatic ring), such as pyridyl groups, pyrimidyl groups and pyrazinyl groups; and amino-substituted aromatic groups (i.e., where the basic nitrogen atom is directly bonded to an aromatic group), such as aminophenyl groups (e.g., —NH—C$_6$H$_4$ and —C$_6$H$_4$—NR$_2$) and aminopyridyl groups.

As employed herein, the term "alkoxy group" encompasses functional groups which include an alkyl-OH, cycloalkyl-OH or aryl-OH functional group whether or not the overall group includes an amino functional group, i.e., an aminofunctional alkoxy groups constitute one type of alkoxy group but not all alkoxy groups necessarily include a basic nitrogen atom.

As illustrated in formula (I) below, the siloxane subunits may not all contain an aminofunctional alkoxy group. Typically, at least a majority and, in many instances, all of the siloxane subunits of the polymer include an aminofunctional alkoxy group. Polysiloxanes where not all of the siloxane subunits of the include the same substituents polymer (with the exception of the terminal subunits) are referred to herein as "polysiloxane copolymers." As used herein, such "copolymers" can have two or more different siloxane subunits. Polysiloxane copolymers can be formed by reacting a mixture of two alcohols, e.g., a mixture of 2-aminoethanol and ethanol, with a polyhydrosiloxane. Generally, the different siloxane subunits are randomly distributed in a polysiloxane copolymer (a "random copolymer"). However, by using appropriate synthetic methods known to those of skill in the art, polysiloxane copolymers in which the different siloxane subunits are present in "blocks" of two or more identical adjacent subunits can also be produced ("block copolymers"). The present polysiloxane copolymers typically have a ratio of siloxane subunits containing an aminofunctional alkoxy group to subunits which do not include an aminofunctional alkoxy group of about 20:1 to 1:20.

Throughout this disclosure, the text refers to various embodiments of the aminofunctional alkoxy polysiloxane compounds and methods of preparing and using the compounds. The various embodiments described are meant to provide illustrative examples and should not necessarily be construed as descriptions of alternative species. Rather it

DETAILED DESCRIPTION

A aminofunctional alkoxy polysiloxane compound can be formed by reacting a linear or cyclic polyhydrosiloxane and an alcohol reactant which includes an aminoalcohol (i.e. an amino functional compound which includes an alkyl-OH, cycloalkyl-OH or aryl-OH functional group) in the presence of a metal catalyst. The reaction of the polyhydrosiloxane and the aminoalcohol is typically carried out in the presence of a dehydrogenative coupling catalyst, such as those catalysts known to be useful for the dehydrogenative coupling of silanes. Suitable dehydrogenative coupling catalysts include catalysts which have been employed in metal catalyzed dehydrogenative coupling of silanes and alcohols, such as those including Cr, Cu, Ir, Mn, Ni, Pd, Pt, Rh, Ru, Ti and Zn species. The dehydrogenative coupling catalysts may be a mixed metal catalyst that includes more than one metal species.

As used in this disclosure, the term "aminofunctional alkoxy polysiloxane" refers to a alkoxy polysiloxane compound which includes one or more aminofunctional alkoxy groups. For the purposes of this application, the term "polyaminofunctional alkoxy group" refers to groups which include two or more amino groups and encompasses groups resulting from the removal of a hydroxyl hydrogen atom from a polyamino functional alkanol (e.g., —O—CH$_2$CH$_2$NH—CH$_2$CH$_2$CH$_2$NH$_2$), a polyamino functional cycloalkanol, a polyamino functional hydroxy-substituted aryl compounds (e.g., —O—C$_6$H$_4$CH$_2$CH$_2$NHCH$_2$CH$_2$NH$_2$).

The method of preparing the aminofunctional alkoxy polysiloxane compound provides for the selective alcoholysis of Si—H bonds with aminoalcohol compounds, without significant degradation of the siloxane backbone or aminolysis of the Si—H bonds (i.e., dehydrogenative coupling of the hydrosilane occurs relatively exclusively with the hydroxyl moiety of the aminoalcohol). Without intending to be limited to any particular theory, it is believed that the formation of the aminofunctional alkoxy polysiloxane is accomplished by the dehydrogenative alcoholysis coupling between the selectively activated Si—H bond of the polyhydrosiloxane and the aminoalcohol.

I. REACTIONS

The formation of the aminofunctional alkoxy polysiloxane can be derived from a "linear" polyhydrosiloxane or a "cyclic" polyhydrosiloxane. An exemplary reaction for the formation of a linear poly((aminofunctional alkoxy)-alkylsiloxane) from a linear polyhydrosiloxane is shown in the following scheme:

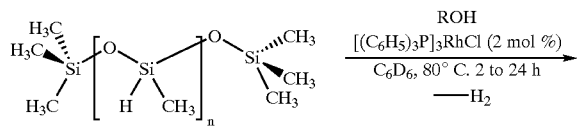

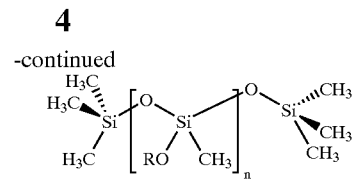

(1) n = 2
(2) n = 32-35
(3) n = 2, R = —CH$_2$CH$_2$CH$_2$NH$_2$
(4) n = 32-35, R = —CH$_2$CH$_2$CH$_2$NH$_2$

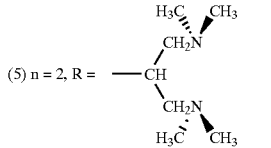

(5) n = 2, R =

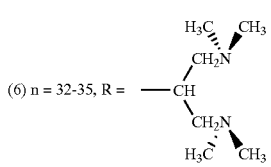

(6) n = 32-35, R =

An exemplary reaction for the formation of a cyclic poly((aminofunctional alkoxy)-alkylsiloxane) from a cyclic polyhydrosiloxane is shown in the following scheme:

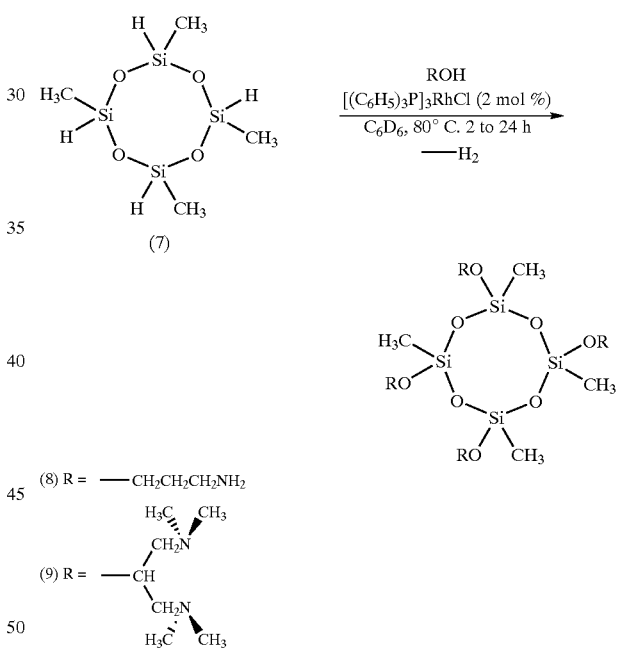

In general, the reaction may be conducted by introducing relatively equimolar amounts of the polyhydrosiloxane and the aminoalcohol (and the catalyst and the optional solvent) into a reaction vessel, and mixing or stirring the components. The reaction between the polyhydrosiloxane and the aminoalcohol is commonly carried out under relatively anhydrous and deoxygenated conditions. This may be conveniently achieved by degassing the reaction mixture and carrying the reaction out under an inert gas atmosphere (e.g. under a dry nitrogen or argon atmosphere). The reaction is typically conducted at a temperature of about 0–200° C. The use of reaction temperatures of less than about 100° C., suitably 60–90° C., is quite common. The reaction mixture may initially become yellow in color and emit gas (presumably H$_2$), and may later became red/orange as the gas emission subsides. The reaction may be conducted for about 1–48 hours, suitably 1–30 hours, suitably 2–12 hours. NMR and IR analysis of the reaction mixture may establish the point at which relatively complete reaction of the Si—H functionalities are achieved. (The reaction progress could be monitored by the residual Si—H and O—H stretches that fall in a convenient window of the IR spectrum, and incorporation ratios of the alcohol can also be determined by integration of the NMR signals assigned to specific components.)

Purification of the product may be achieved by passing the polyalkoxysiloxane product through neutral silica gel. In some instances, it may be advantageous to place a layer of anhydrous magnesium sulfate on top of a silica gel plug used to purify the reaction product. In another embodiment, the catalyst may be precipitated, (e.g., by allowing a benzene solution of the product to stand at ambient temperature for about 24–48 hours) and then removed by filtration.

II. POLY(HYDROSILOXANE)

Exemplary polyhydrosiloxanes which can be used as starting materials in the present method include polyhydrosiloxane (linear and/or cyclic) with one or two Si—H bonds in each siloxane subunit. The polyhydrosiloxane may be an alkyl, aryl and/or aralkyl substituted polysiloxane. Particularly suitable compounds are polyalkylhydrosiloxanes substituted with lower alkyl groups (i.e. $C_1$–$C_{10}$ alkyl groups), such as methyl and/or ethyl groups. Other suitable polyhydrosiloxanes may be substituted with alkyl, cycloalkyl, phenyl and/or benzyl groups.

Examples of suitable linear polyhydrosiloxane for use in the present method include compounds having the formula (I):

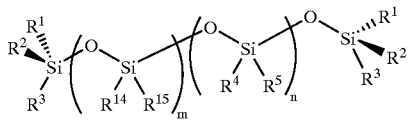

wherein n is an integer from 2 to 1,000 and m is an integer from 0 to 1,000;

$R^1$, $R^2$ and $R^3$ are independently $C_1$–$C_{10}$ alkyl, cyclopentyl, cyclohexyl, benzyl, toluyl, xylyl or phenyl;

$R^4$ is $C_1$–$C_{10}$ alkyl, cyclopentyl, cyclohexyl, benzyl, toluyl, xylyl, or phenyl;

$R^5$ is hydrogen;

$R^{14}$ is hydrogen, $C_1$–$C_{10}$ alkyl, cyclopentyl, cyclohexyl, benzyl, toluyl, xylyl, or phenyl; and $R^{15}$ is hydrogen, $C_1$–$C_{10}$ alkyl, cyclopentyl, cyclohexyl, benzyl, toluyl, xylyl, or phenyl.

In one common embodiment, $R^1$, $R^2$ and $R^3$ are independently $C_1$–$C_6$ alkyl, $R^4$ is a methyl group, and $R^{14}$ and $R^{15}$ are independently hydrogen or methyl. In polyhydrosiloxanes of this type, individual siloxane subunits are typically substituted with a random distribution of (a) a hydrogen and an alkyl group; (b) two alkyl groups; and (c) two hydrogen atoms. The polyalkoxysiloxane products formed from such a polyhydrosiloxane will generally have a corresponding random distribution of substituents where some or all (depending on the stoichiometry of the reactants) of the hydrogen atoms of the polyhydrosiloxane have been replaced by an alkoxy group. Specific examples of suitable linear polyalkysiloxane compounds include such compounds where $R^1$, $R^2$ and $R^3$ are methyl groups and n and m are integers from 2 to about 100.

Examples of suitable cyclic polyhydrosiloxane compounds for use in the present method include compounds having the following formula (II):

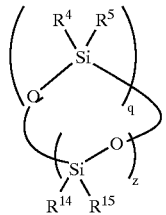

wherein q is an integer from 1 to 12; z is an integer from 0 to 11; and q+z=an integer from 3 to 12;

$R^4$ is $C_1$–$C_{10}$ alkyl cyclopentyl, cyclohexyl, benzyl, toluyl, xylyl, or phenyl;

$R^5$ is hydrogen;

$R^{14}$ is hydrogen, $C_1$–$C_{10}$ alkyl, cyclopentyl, cyclohexyl, benzyl, toluyl, xylyl, or phenyl; and $R^{15}$ is hydrogen, $C_1$–$C_{10}$ alkyl, cyclopentyl, cyclohexyl, benzyl, toluyl, xylyl, or phenyl.

Specific examples of suitable cyclic polyalkoxysiloxane compounds include compounds where z is 0 and $R^4$ is methyl, such as cyclotetra(methylhydro)-siloxane ("D4H"; n=4) and cyclodeca(methylhydro)-siloxane ("D10H"; n=10).

III. AMINOALCOHOL

The alcohol reactant employed in the present method includes an aminoalcohol or a polyaminoalcohol. Depending on the desired product, the alcohol reactant may only include aminoalcohol or may be a mixture of aminoalcohol and an alcohol compound lacking an amino functional group. For example, the alcohol reactant may be a mixture of 3-aminopropanol and ethanol.

The aminoalcohol includes at least one amino group, which is an organic functional group including a basic nitrogen atom. The amino group may be a primary, secondary or tertiary amino group. Examples of suitable amino groups include aliphatic amino groups (e.g. mono-, di- and trialkyl amino groups), cycloaliphatic amino groups (e.g. piperidinyl and piperazinyl groups), heterocyclic amino groups (e.g. pyridyl groups, pyrimidyl groups and pyrazinyl groups), and aromatic amino groups (e.g. anilino groups and aminophenyl groups). As used in this disclosure, the term "aminoalcohol" includes amino functional hydroxy substituted alkyl, cycloalkyl, aralkyl and aryl compounds.

The aminoalcohol is suitably an aminofunctional alkoxy alcohol, which provides an aminofunctional alkoxy group to the poly((aminofunctional alkoxy)-alkylsiloxane). Specific examples of suitable aminoalcohols include 3-amino-1-propanol, 1,3-(N,N-dimethylamino)-2-propanol, 2,5-dimethoxybenzyl alcohol, 3-(2-pyridyl)-1-propanol, 3-(4-pyridyl)-1-propanol, 4-hydroxy-N-methylpiperidine, 4-aminophenol, and 9-phenanthrolinemethanol. The amino functional group may be "pendant" on the alkoxy group (i.e. not in the backbone chain of the alkoxy group) and/or present as part of the backbone chain of the alkoxy group.

As discussed above, the alcohol may be a mixture of an aminoalcohol and plain alcohol (i.e., an alcohol compound lacking an amino functional group). Specific examples of the suitable mixture of the aminoalcohol and plain alcohol include a 50:50 mixture of HO—(CH$_2$)$_3$—NH$_2$ and ethanol (CH$_3$CH$_2$OH). Without intending to be limited to any particular theory, it is believed that using a mixture of the aminoalcohol and plain alcohol would result in a suitable poly((aminofunctional alkoxy)-alkylsiloxane) compound, and the number of amino groups present relative to the number of siloxane subunits would be less than typically achieved with only an aminoalcohol. According to a preferred embodiment, the alcohol is a primary alcohol. According to an alternative embodiment the alcohol may be relatively hindered (e.g. tert-butyl alcohol).

IV. CATALYST

The reaction of the polyhydrosiloxane and the alcohol reactant is typically carried out in the presence of a catalyst. The catalyst may be provided in an amount of less than about 5 mole %, suitably less than about 0.1 mole %, suitably less than about 0.01 mole %. The amount of catalyst employed can be determined by those of skill in the art and will be based on a variety of factors such as desired reaction time, type of metal species in the catalyst, the presence or absence of solvent in the reaction mixture, the particular reactants involved, the configuration of the reaction vessel and the like.

The reaction of the polyhydrosiloxane and the aminoalcohol is typically carried out in the presence of a dehydrogenative coupling catalyst, such as those catalysts known to be useful for the dehydrogenative coupling of silanes. Suitable dehydrogenative coupling catalysts include catalysts which have been employed in metal catalyzed dehydrogenative coupling of silanes and alcohols, such as those including Pd, Cu, Mn, Ni, Rh and/or Ru species. Other suitable dehydrogenative coupling catalysts may include Pt, Zn, Ir, Cr, and/or Ti species. The dehydrogenative coupling catalysts may be a mixed metal catalyst that includes more than one metal species.

Particularly suitable catalysts include rhodium catalysts and, more desirably, catalysts which include rhodium(I) species, such as phosphine-containing rhodium(I) catalysts. Suitable examples of phosphine-containing rhodium(I) catalysts include tris-phosphino rhodium(I) salts, such as RhCl(P(C$_6$H$_5$)$_3$)$_3$ (known as "Wilkinson's catalyst"), RhCl(P(CH$_2$CH$_2$(CF$_2$)$_{n=6-8}$CF$_3$)$_3$)$_3$ and RhCl(P(C$_6$H$_{11}$)$_3$)$_3$. Examples of additional suit rhodium catalysts include the compounds shown in Table 1:

TABLE 1

| | |
|---|---|
| (η$^6$-C$_6$H$_6$B(C$_6$H$_6$)$_3$)Rh(cod) | Rh(CO)$_2$(acac) |
| ((C$_8$H$_{14}$)$_2$RhCl)$_2$ | Rh(cod)B(C$_6$H$_5$)$_4$ |
| ({RhCl(CH$_2$=CH$_2$)$_2$}$_2$) | Rh(C$_8$H$_{12}$)$_2$BF$_4$/P(C$_6$H$_5$)$_3$ |
| (RhCl$_2$(CO)$_2$)$_2$ | Rh$_2$CO$_2$(CO)$_{12}$ |
| 5% Rh/C | Rh$_4$(CO)$_{12}$ |
| CO$_2$Rh$_2$(CO)$_2$ | Rh$_4$(CO)$_{12}$/NEt$_3$ |
| Rh/Al$_2$O$_2$ | Co$_3$Rh(CO)$_{12}$ |
| Rh/C | |

Other suitable catalysts include those catalysts useful for metal catalyzed dehydrogenative coupling of silanes and alcohols including Pd, Cu(0), Cu(I), Cu(II), Mn, Pd(0), Ni and Ru metal species. Specific examples of such catalysts for catalyzed dehydrogenative coupling of silanes and aminoalcohols include compounds having the formula as shown in Table 2:

TABLE 2

| | |
|---|---|
| 10% Pd/C | H$_3$SiMn(CO)$_5$ |
| Cu(O) metal | Mn$_2$(Co)$_{10}$ |
| CuCl/LiO(t-C$_4$H$_9$) | Pd/C |
| CuClCN/LiO(t-C$_4$H$_9$) | PdCl$_2$(P(C$_6$H$_5$)$_3$)$_3$ |
| CUO(t-C$_4$H$_9$)/(C$_4$H$_9$)$_4$NCl | Raney Ni |
| RUCl$_2$(P(C$_6$H$_5$)$_3$)$_3$ | |
| tris(dibenzylideneacetone)dipalladium(0)-chloroform | |

Still other suitable catalysts include those catalysts useful for the dehydrogenative coupling of silanes, specifically those including U, Mn, Pd, Pt, Ni and Ru metal secies. Specific examples of suitable catalysts for dehydrogenative coupling of silanes include compounds having the formula as shown in Table 3:

TABLE 3

| | |
|---|---|
| ((Et$_2$N)$_3$U)(B(C$_6$H$_6$)$_4$) | Pd/C |
| H$_3$SiMn(CO)$_5$ | Pd(OCOCH$_3$)$_2$ |
| Pd/Al$_2$O$_2$ | PdCl$_2$((C$_2$H$_5$)$_3$P) |
| Raney Ni | Pt/C |
| Ru/C | |

Still other suitable catalysts include those catalysts having Mn, Pt, Ir, Ti, Ni, Au, Cr, Fe, Pd, Ir, Mo, Ru, Y, Zn and Ru metal species shown in Table 4 below:

TABLE 4

| | |
|---|---|
| (CO)$_5$MnC(O)(C$_6$H$_5$) | IrCl(CO)((C$_6$H$_5$)$_3$P)$_2$ |
| (CO)$_5$MnC(O)CH$_3$ | IrCl$_3$ |
| (CO)$_5$MnSi(CH$_3$)$_2$(C$_6$H$_5$) | K$_2$PtCl$_4$ |
| ((C$_6$H$_5$)$_3$P)$_2$Ir(CO)Cl | Mn$_2$(CO)$_{10}$ |
| ((C$_6$H$_5$)$_3$P)$_2$PtCl$_2$ | MO(CO)$_6$ |
| ((C$_6$H$_5$)P)(CO)$_4$MnBr | Ni(cod)$_2$ |
| ((C$_6$H$_5$)P)(CO)$_4$MnC(O)CH$_3$ | NiCl$_2$ |
| ((CH$_3$CH$_2$CH$_2$CH$_2$)$_3$P)$_2$PtCl$_2$ | NiCl$_2$/(C$_6$H$_5$)SH |
| ((cyclohexyl)$_3$P)Pt(ethene)$_2$ | NiCl$_2$/(CH$_3$CH$_2$)$_2$S |
| (μ-OTi(salen))$_2$ | NiCl$_2$/CS$_2$ |
| ((t-butyl)$_3$P)Pt(divinyldimethoxysilane) | NiI$_2$/Li |
| ((t-butyl)$_3$P)Pt(norbornene)$_2$ | NiI$_2$/Li |
| AuCl(P(C$_6$H$_5$)$_3$) | Pd/C |
| Bis(benzene)chromium(0) | PdCl$_2$(PEt$_3$)$_2$ |
| Ethylenebis(tetrahydroindenyl) TiF$_2$ | Pt/C |
| Zn(Zn(C$_2$H$_5$)$_2$/diamine | Pt(acac)$_2$ |
| H$_2$ + Pd/C | Pt-black |
| H$_2$PtCl$_6$*6H$_2$O | RUCl$_2$(P(C$_6$H$_5$)$_3$)$_3$ |
| Zn(2-ethylhexanoate)$_2$/NaBH$_4$ | RuCl$_3$ |
| Ycl$_3$ | RuCl$_3$*nH$_2$O/CH$_3$CN |
| Fe(CO)$_5$ | RuHCl(CO)(i-C$_3$H$_7$)$_3$P)$_2$ |

Ethylene-bis(indenyl)Ti(1,1'-binapth-2,2'-diolate)
Ethylene-bis(indenyl)Ti(1,1'-binapth-2,2'-diolate)
Y(2,2'-bis-(tert-butyldimethylsilylamido)-6,6'-dimethylbiphenyl)(CH$_3$)(THF)$_2$
(Ni{η-CH$_2$=CHSiMe$_2$)$_2$O}$_2${μ-(η-CH$_2$=SiMe$_2$)$_2$O})

V. SOLVENT

Depending on the choice of starting materials, the reaction may be "neat" (i.e. without added solvent) or in the presence of a solvent. In cases where the starting poly (alkylhydrosiloxane) is somewhat viscous, it is typically advantageous to include a solvent in the reaction mixture. The solvent is desirably chosen so that it does not react with other components of the reaction mixture and, preferably, does not strongly interact with the catalyst (if one is present). Exemplary solvents include relatively inert solvents that are capable of solublizing the reactants, such as hydrocarbon solvents, halogenated hydrocarbon solvents, and ethers.

Suitable solvents include, without limitation, aromatic solvents (e.g. benzene, toluene, xylene, chlorobenzene and the like), hydrocarbon solvents (e.g. hexanes, heptanes, octanes, petroleum fractions), halogenated alkanes (e.g. $CCl_4$, chlorinated ethanes, and the like), ethers (e.g. dialkyl ethers, glymes, THF, and the like).

VI. AMINOFUNCTIONAL ALKOXY POLYSILOXANES

A aminofunctional alkoxy polysiloxane may be formed from a polyhydrosiloxane and an aminoalcohol. The aminofunctional alkoxy polysiloxane may be linear or cyclic, depending on the nature of the polyhydrosiloxane selected.

Examples of suitable linear aminofunctional alkoxy polysiloxane compounds that may be produced by the method include compounds having the formula (III):

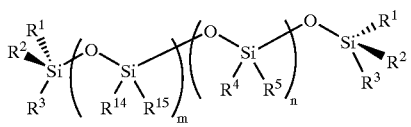

wherein n is an integer from 2 to 1,000 and m is an integer from 0 to 1,000;

$R^1$, $R^2$ and $R^3$ are independently $C_1$–$C_6$ alkyl, cyclopentyl, cyclohexyl, benzyl, toluyl, xylyl or phenyl;

$R^4$ is hydrogen, $C_1$–$C_{10}$ alkyl, cyclopentyl, cyclohexyl, benzyl, toluyl, xylyl, phenyl or an alkoxy group;

$R^5$ is an aminofunctional alkoxy group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl, or an alkoxy group.

More commonly, $R^1$, $R^2$ and $R^3$ are independently $C_1$–$C_6$ alkyl and, preferably, methyl groups, and $R^4$, $R^{14}$ and $R^{15}$ are independently hydrogen, phenyl or methyl. Specific examples of suitable linear poly((aminofunctional alkoxy)-alkylsiloxane) compounds that may be produced by the present method include compounds having the formula (IV):

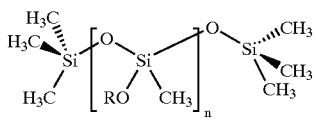

(1) n = 2; R = $CH_2CH_2CH_2NH_2$ (Data Complete)
(2) n = 32–35; R = $CH_2CH_2CH_2NH_2$
(3) n = 2, R = $CH_2CH_2NHCH_2CH_2NH_2$
(4) n = 32–35; R = $CH_2CH_2NHCH_2CH_2NH_2$

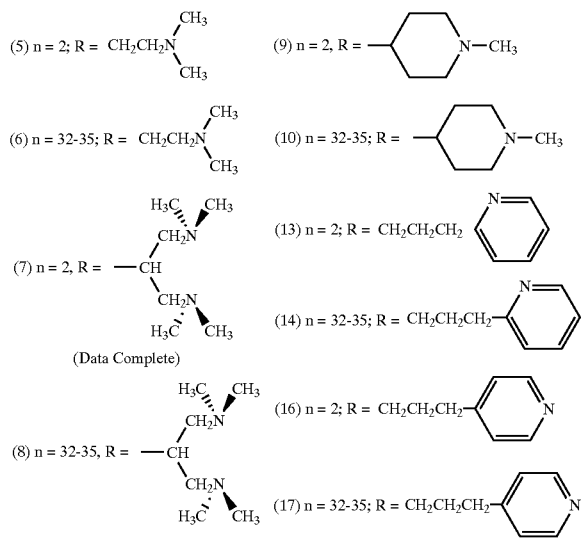

Examples of suitable cyclic aminofunctional alkoxy polysiloxane compounds that may be produced by the method include compounds having the formula (V):

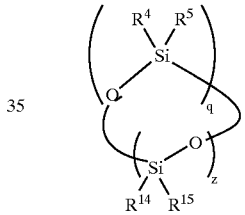

wherein q is an integer from 1 to 12; z is an integer from 0 to 11; and q+z=an integer from 3 to 12;

$R^4$ is hydrogen, $C_1$–$C_{10}$ alkyl, cyclopentyl, cyclohexyl, benzyl, toluyl, xylyl, phenyl or an alkoxy group;

$R^5$ is an aminofunctional alkoxy group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl or an alkoxy group.

Specific examples of suitable cyclic poly(aminofunctional alkoxy)-alkylsiloxane) compounds that may be produced by the method include compounds having the formula (VI):

(VI)

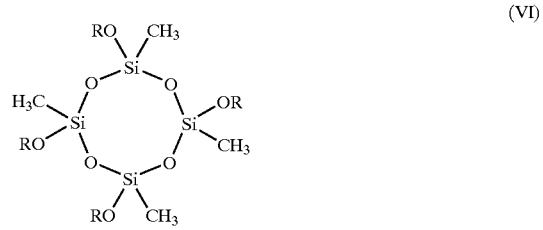

where R— is an aminofunctional alkyl group, e.g., compounds having the formula (VI) where R is:

R = —CH$_2$CH$_2$CH$_2$NH$_2$ (20)

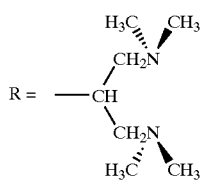 (21)

R = —CH$_2$CH$_2$NHCH$_2$CH$_2$NH$_2$ (22)

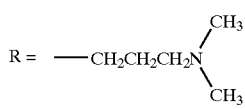 (23)

Suitable aminofunctional alkoxy polysiloxane compounds may be derived by selecting the appropriate aminoalcohol (i.e. the aminoalcohol selected corresponds to the alkoxy group of the aminofunctional alkoxy polysiloxane compound).

The amino group of the aminofunctional alkoxy polysiloxane compounds may be aliphatic or cycloaliphatic. Specific examples of suitable alkoxy groups of the aminofunctional alkoxy polysiloxane compound include groups corresponding to an aliphatic aminoalcohol represented by the formulas:

HOCH$_2$CH$_2$CH$_2$NH$_2$

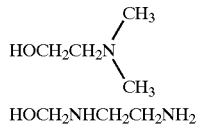

HOCH$_2$NHCH$_2$CH$_2$NH$_2$

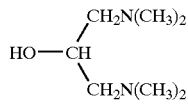

The aminofunctional group of the aminofunctional alkoxy polysiloxane compounds may include a piperidinyl group, a piperazinyl group and a pyrrolidinyl group. The aminofunctional group of the aminofunctional alkoxy polysiloxane compounds may include an aromatic amino group. Examples of suitable aromatic amino groups of the aminofunctional alkoxy polysiloxane compounds can include a pyridyl group, a pyrimidyl group and/or a pyrazinyl group. The aminofunctional group of the aminofunctional alkoxy polysiloxane compounds may include an amino-substituted aromatic group such as anilino groups and aminophenyl groups.

The aminofunctional group of the aminofunctional alkoxy polysiloxane compounds may include diaminofunctional alkoxy groups. The diaminofunctional groups may be a 1,2-diaminofunctional alkoxy group and a 1,3-diaminofunctional alkoxy group. Suitable examples of diaminofunctional alkoxy groups include 1,3-diaminofunctional alkoxy groups having the formula (VII):

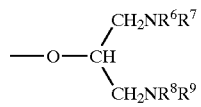 (VII)

wherein $R^6$, $R^7$, $R^8$ and $R^9$ are independently hydrogen or $C_1$–$C_6$ alkyl, or $R^6$ and $R^7$ form a $C_3$–$C_8$ cyclic group or $R^8$ and $R^9$ form a $C_3$–$C_8$ cyclic group. Specific examples of such 1,3-diaminofunctional alkoxy groups include

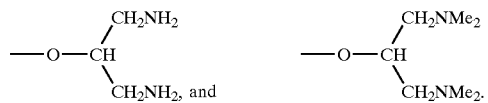

Specific examples of suitable alkoxy groups of the aminofunctional alkoxy polysiloxane compound corresponding to a diaminofunctional include groups having the formula (VIII):

—O—CH$_2$CH$_2$NR$^7$(CH$_2$)$_q$NR$^8$R$^9$ (VIII)

where q is 2 or 3; and $R^7$, $R^8$ and $R^9$ are independently hydrogen or $C_1$–$C_6$ alkyl, or $R^8$ and $R^9$ form a $C_3$–$C_8$ cyclic group. Specific examples of such diaminofunctional groups include groups represented by the formulas:

| (1) —O—CH$_2$CH$_2$NHCH$_2$CH$_2$NMe$_2$ | (4) —O—CH$_2$CH$_2$NHCH$_2$CH$_2$CH$_2$NMe$_2$ |
| (2) —O—CH$_2$CH$_2$NMeCH$_2$CH$_2$NMe$_2$ | (5) —O—CH$_2$CH$_2$NMeCH$_2$CH$_2$CH$_2$NMe$_2$ |
| (3) —O—CH$_2$CH$_2$NHCH$_2$CH$_2$NH$_2$ | (6) —O—CH$_2$CH$_2$NHCH$_2$CH$_2$CH$_2$NH$_2$ |

The amino functional substituent that may be present in the aminofunctional alkoxy polysiloxane compounds could include heteroatoms in the backbone of the substituent itself according to suitable embodiments. Suitable examples of such heteroatoms in the backbone of the amino functional alkoxy substituent include compounds represented by the formulas:

—(O—CHR—CH$_2$)$_n$—NH$_2$ (1)

—(O—CHR—CH$_2$)$_n$—NHR (2)

—(O—CH$_2$—CH$_2$)$_n$—NR$_2$ (3)

The poly((aminofunctional alkoxy)-alkylsiloxane) compounds are typically a liquid at room temperature, and have a viscosity less than about the viscosity of water. The poly((aminofunctional alkoxy)-alkylsiloxane) compounds are generally transparent and colorless.

The poly((aminofunctional alkoxy)-alkylsiloxane) compounds generally have relatively good stability. For example, the poly((aminofunctional alkoxy)-alkylsiloxane) compounds are commonly stable for about five weeks at ambient temperature under an inert atmosphere (e.g. gas), and stable for about one day at ambient temperature and pressure. Stability of at least about several months may be achieved for the poly((aminofunctional alkoxy)-alkylsiloxane) compounds by storage under refrigeration (e.g. temperature less than about 10° C.).

The aminofunctional alkoxy group typically includes no more than about 30 carbon atoms. The poly ((aminofunctional alkoxy)-alkylsiloxane) compounds typically have a relatively high solubility in common organic solvents (which facilitates characterization by NMR, IR and UV), and relatively good solubility in water. The poly ((aminofunctional alkoxy)-alkylsiloxane) may be a homopolymer, a blend, or a stoichiometric copolymer according to alternative embodiments.

VII. UTILITY

Poly((aminofunctional alkoxy)-alkylsiloxane) compounds can have a variety of uses. For example, such compounds may be useful as a component of a coating composition. Depending on the particular application, a poly((aminofunctional alkoxy)-alkylsiloxane) compound may be used by itself to form a coating or may be formulated with other components known to those of skill in the art to form the coating composition. For example, a poly ((aminofunctional alkoxy)-alkylsiloxane) may act as a crosslinking agent and/or curing accelerator in a coating composition, e.g., in an epoxy-based coating composition.

In another embodiment, a poly((aminofunctional alkoxy)-alkylsiloxane) compound may be used as a "primer" component in a coating system (e.g. to adhere a topcoat to a substrate). The primer containing the poly ((aminofunctional alkoxy)-alkylsiloxane) and a topcoat (e.g. polyurethane may be applied to a substrate according to the following exemplary method. A substrate (e.g. aluminum 2024-T3) may be treated by cleaning its surface with a solvent (e.g. acetone). The primer may be applied to the substrate "neat" with an applicator such as a "draw down" bar. The primer may be dried at ambient temperature for about one day, and cured at about 45 C for about five hours. The topcoat may be applied to the primer with an applicator such as a "draw down" bar. The topcoat may be dried at ambient temperature for about one day, and subsequently cured at an elevated temperature (e.g. at about 45–50 C for a period of hours).

Other uses for the poly((aminofunctional alkoxy)-alkylsiloxane) compounds include applications in the production of adhesives, catalyst supports, ionically conductive materials, liquid crystals, crosslinking agents, conductive and electroluminescent polymers, electrochemical sensing devices, and nonlinear optical chromophores.

VIII. EXAMPLES

In Examples 1–6, a poly((aminofunctional alkoxy)-alkylsiloxane) was formed by reacting a poly (alkylhydrosiloxane) and an aminoalcohol in deuterobenzene in the presence of a Rh(I) catalyst ((($C_6H_5$)$_3$P)$_3$RhCl). Two methods were used to remove the spent catalyst. According to the first method ("Method A"), the reaction mixture was flushed through a ml syringe having a "Kimwipe" plug at the bottom, followed by a 3 ml silica gel plug (i.e. neutral, dried under vacuum and subsequently saturated with either benzene or toluene). On the occasions that excess aminoalcohol was present in the product mixture, it was removed by flushing the product mixture through a silica-gel plug (1 in.×1 cm diameter, with toluene solvent) where the aminoalcohol could be isolated as a secondary eluent. According to the second method ("Method B"), the reaction mixture was allowed to sit for about two days at ambient temperature, after which the catalyst precipitated out of solution as a red solid. The supernate was then removed from the solid with a syringe.

For Examples 1–6, all operations were carried out under inert atmosphere (unless otherwise stated). Deuterated benzene ($C_6D_6$) was purchased from Cambridge Isotope Laboratories, Inc. of Andover, Mass. and distilled over sodium under inert atmosphere prior to use. All other reagents were purchased from Sigma Aldrich Chemical Co., Inc. of Milwaukee, Wis. and used without further purification. $^1$H and $^{29}$Si NMR spectra for the product were obtained on a Varian Inova 400 MHz NMR commercially available from Varian, Inc. of Palo Alto, Calif. $^{13}$C NMR spectra for the product were obtained on a Varian Mercury 300 MHz NMR commercially available from Varian, Inc. of Palo Alto, Calif. NMR chemical shifts were referenced to a tetramethylsilane δ=0.00 ppm) external standard. Infrared analysis were performed using liquid cells on a Mattson 2020 series FT-Infrared Spectrometer commercially available from Mattson Instruments of Madison, Wis.

Example 1 bis-(Trimethylsiloxy)-1,3-dimethyl-1,3-(3-amino-1-propoxy)siloxane

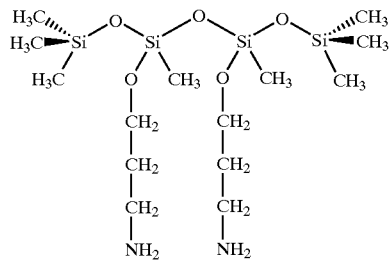

Deuterobenzene (1 ml), 3-amino-1-propanol (1.51 ml, 0.02 mol), and (($C_6H_5$)$_3$P)$_3$RhCl (0.162 g, 0.0002 mol) were introduced into a 25 ml "Schlenk" tube containing a magnetic stirring bar and sealed with a rubber septum. These components were degassed via 5 freeze/pump/thaw cycles and infused with argon. 1,3-Bis(trimethyl-siloxy)-1,3-dimethylsiloxane (3.30 ml, 0.02 mol) was injected into the reaction tube via a syringe while the other reactants were still frozen (to minimize autocatalization by the amine moieties) and 5 additional freeze/pump/thaw cycles were performed in order to further de-gas the reaction mixture.

At this time, the reaction tube was submerged in a silicon oil bath preheated to 80° C. As all of the reactants became homogenous, the reaction mixture became bright yellow in color and vigorous gas evolution (presumably $H_2$) was observed. The reaction tube was kept under positive argon pressure during the entire course of the reaction in order to flush the $H_2$ gas from the reaction mixture. After approximately 1 hour, the reaction mixture became red/orange and the gas evolution subsided, the solution was stirred at 80° C. for an additional hour to ensure substantially complete conversion. NMR and IR samples were extracted via a syringe and indicated complete conversion.

After using Method A or Method B, the catalyst could not be detected by NMR in the product solution (catalyst arene substituent $^1H$ δ=7.17 m, 7.65 m; $^{13}C$ δ=128.92, 129.08, 132.14, 132.60, 132.723). The solvent was removed via reduced pressure. The isolated yield of the product using Method A was 72%, while the isolated yield of the product from Method B was 95%.

The $^1H$ NMR spectra for the product were as follows: $^1H$ δ=0.104 (s, 1H, —OSi(CH$_3$)$_3$), 0.08 (s, 3H, —OSi(CH$_3$) (OCH$_2$CH$_2$CH$_2$NH$_2$)O—), 0.78 (bs, 2H, —OCH$_2$CH$_2$CH$_2$NH$_2$), 1.52 (p, 2H, —OCH$_2$CH$_2$CH$_2$NH$_2$, $J_{2-1}$=6.35 Hz, $J_{2-3}$=6.61 Hz), 2.63 (t, 2H, —OCH$_2$CH$_2$CH$_2$NH$_2$, $J_{2-3}$=6.61 Hz), 3.74 (t, 2H, —OCH$_2$CH$_2$CH$_2$NH$_2$, $J_{1-2}$=6.35 Hz).

The $^{13}C$ NMR spectra for the product were as follows: $^{13}C$ δ=-4.14 (—OSi(CH$_3$)(OCH$_2$CH$_2$CH$_2$NH$_2$)O—), 1.43 (—OSi(CH$_3$)$_3$), 36.31 (—OCH$_2$CH$_2$CH$_2$NH$_2$), 38.85 (—OCH$_2$CH$_2$CH$_2$NH$_2$), 59.88 (—OCH$_2$CH$_2$CH$_2$NH$_2$).

The $^{29}Si$ NMR spectra for the product were as follows: $^{29}Si$ δ=-57.74 & -57.77 (rac & meso diads —OSi(CH$_3$) (OCH$_2$CH$_2$CH$_2$NH$_2$)O—), 8.65 and 8.62 (rac and meso diads, —OSi(CH$_3$)$_3$).

The FT-Infrared spectra (in C$_6$D$_6$) for the product were as follows: —NH$_2$ absorbances at 3391 cm$^{-1}$ and 3310 cm$^{-1}$.

Example 2

Poly((3-amino-1-propoxy)methylsiloxane)

In a 25 ml "Schlenk" tube, 3-amino-1-propanol (1.51 ml, 0.02 mol) and ((C$_6$H$_5$)$_3$P)$_3$RhCl (0.162 g, 0.0002 mol) were mixed in deuterobenzene (1 ml) and sealed with a rubber septum. These components were degassed via 5 freeze/pump/thaw cycles and infused with argon. Poly (methylhydro)siloxane (1.21 ml, 0.02 mol) was injected into the reaction tube via a syringe, while the other reactants were still frozen and 5 additional freeze/pump/thaw cycles were performed in order to further de-gas the reaction mixture.

At this time, the reaction tube was submerged in a silicon oil bath preheated to 80° C. As all of the reactants became homogenous, the reaction mixture became bright yellow in color and vigorous gas evolution (presumably H$_2$) was observed. The reaction tube was kept under positive argon pressure during the entire course of the reaction in order to flush the H$_2$ gas from the reaction mixture. After approximately 1 hour, the reaction mixture became red/orange, and the gas evolution subsided. The solution was stirred at 80° C. for an additional hour (e.g. for substantially complete conversion). NMR and IR samples were extracted via a syringe and indicated substantially complete conversion of Si—OH and OH bonds.

The reaction mixture was allowed to sit for about two days at ambient temperature, after which the catalysts had precipitated out of solution as a red solid. The supernate was removed from the solid with a syringe (isolated yield of the product was 94%).

The $^1H$ NMR spectra for the product were as follows: $^1H$ δ=0.09 (bs, 3H, —OSi(CH$_3$)(OCH$_2$CH$_2$CH$_2$NH$_2$)O—), 0.22 (bs, approx. 1H, —OSi(CH$_3$)$_3$), 0.87 (bs, 2H, —OCH$_2$CH$_2$CH$_2$NH$_2$), 1.58 (bs, 2H, —OCH$_2$CH$_2$CH$_2$NH$_2$), 2.67 (bs, 2H, —OCH$_2$CH$_2$CH$_2$NH$_2$), 3.81 (bs, 2H, —OCH$_2$CH$_2$CH$_2$NH$_2$).

The $^{13}C$ NMR spectra for the product were as follows: $^{13}C$ δ=-2.50 to -5.70 (multiple peaks, —OSi(CH$_3$) (OCH$_2$CH$_2$CH$_2$NH$_2$)O—), 1.61 (—OSi(CH$_3$)$_3$), 35.50 (—OCH$_2$CH$_2$CH$_2$NH$_2$), 38.99 (—OCH$_2$CH$_2$CH$_2$NH$_2$), 60.36 (—OCH$_2$CH$_2$CH$_2$NH$_2$).

The $^{29}Si$ NMR spectra for the product were as follows: $^{29}Si$ δ=-57.4 to -58.4 (multiple peaks, —OSi(CH$_3$)(OCH$_2$CH$_2$CH$_2$NH$_2$)O—), 8.88 to 9.05 (multiple peaks, —OSi(CH$_3$)$_3$).

The FT-Infrared spectra (in C$_6$D$_6$) for the product were as follows: —NH$_2$ absorbances at 3391 cm$^{-1}$ and 3310 cm$^{-1}$.

Example 3 bis-(Trimethylsiloxy)-1,3-dimethyl-1,3-(1,3-N,N-dimethylamino)-2-propoxy)siloxane

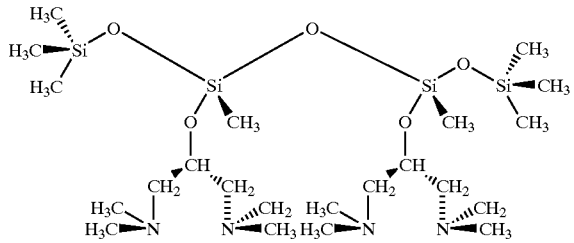

Bis(trimethylsiloxy)-1,2-dimethyl-1,2-(1,3-(N,N-dimethylamino)-2-propoxy)siloxane was synthesized according to the method described in Example 2, except that N,N-1,3-dimethylamino,2-propanol (3.26 ml, 0.02 mol) was used instead of 3-amino-1-propanol. Method B was used to isolate the product in 97% yield.

The $^1H$ NMR spectra for the product were as follows: $^1H$ δ=0.22 (s, 24H, —OSi(CH$_3$)$_3$), 0.26 (s, 6H, —OSi(CH$_3$) ((CH$_3$)$_2$NCH$_2$CH(—O)CH$_2$N(CH$_3$)$_2$)O—), 2.22 (s, 12H, (CH$_3$)$_2$NCH$_2$CH(—O)CH$_2$N(CH$_3$)$_2$), 2.44 (dm, 4H, (CH$_3$)$_2$NCH$_2$CH(—O)CH$_2$N(CH$_3$)$_2$), 4.15 (p, 1H, (CH$_3$)$_2$NCH$_2$CH(—O)CH$_2$N(CH$_3$)$_2$).

The $^{13}C$ NMR spectra for the product were as follows: $^{13}C$ δ=-2.53 (—OSi(CH$_3$)(CH$_3$)$_2$NCH$_2$CH(—O)CH$_2$N (CH$_3$)$_2$)O—), 1.87 (—OSi(CH$_3$)$_3$), 46.55 ((CH$_3$)$_2$NCH$_2$CH (—O)CH$_2$N(CH$_3$)$_2$), 64.32 ((CH$_3$)$_2$NCH$_2$CH(—O)CH$_2$N (CH$_3$)$_2$), 69.99 ((CH$_3$)$_2$NCH$_2$CH(—O)CH$_2$N(CH$_3$)$_2$).

The $^{29}Si$ NMR spectra for the product were as follows: $^{29}Si$ δ=-59.34 and -58.40 (rac and meso diads, —OSi(CH$_3$) ((CH$_3$)$_2$NCH$_2$CH(—O)CH$_2$N(CH$_3$)$_2$)O—), 7.99 & 7.74 (rac and meso diads, —OSi(CH$_3$)$_3$).

Example 4

Poly((1,3—N,N-dimethylamino-2-propoxy) methylsiloxane)

Poly((1,3-N,N-dimethylamino-2-propoxy) methylsiloxane was synthesized according to the method described in Example 2, except that 1,3-N,N-dimethylamino-2-propanol (3.26 ml, 0.02 mol) was used instead of 3-amino-1-propanol. Method B was used to isolate the product in 97% yield.

The $^1H$ NMR spectra for the product were as follows: $^1H$ δ=0.25 (s, 24H, —OSi(CH$_3$)$_3$), 0.38 (s, 6H, —OSi(CH$_3$) ((CH$_3$)$_2$NCH$_2$CH(—O)CH$_2$N(CH$_3$)$_2$)O—), 2.22 (s, 12H, CH$_3$)$_2$NCH$_2$CH(—O)CH$_2$N(CH$_3$)$_2$), 2.44 (dm, 4H, (CH$_3$)$_2$NCH$_2$CH(—O)CH$_2$N(CH$_3$)$_2$), 4.42 (p, 1H, (CH$_3$)$_2$NCH$_2$CH(—O)CH$_2$N(CH$_3$)$_2$).

The $^{13}C$ NMR spectra for the product were as follows: $^{13}C$ δ=-2.72 (—OSi(CH$_3$)(CH$_3$)$_2$NCH$_2$CH(—O)CH$_2$N (CH$_3$)$_2$)O—), 1.87 (—OSi(CH$_3$)$_3$), 46.73 ((CH$_3$)$_2$NCH$_2$CH (—O)CH$_2$N(CH$_3$)$_2$), 64.59 ((CH$_3$)$_2$NCH$_2$CH(—O)CH$_2$N(CH$_3$)$_2$), 70.02 ((CH$_3$)$_2$NCH$_2$CH(—O)CH$_2$N(CH$_3$)$_2$).

The $^{29}$Si NMR spectra for the product were as follows: $^{29}$Si δ=−58.0 to −61.0 (multiple peaks, —OSi(CH$_3$)((CH$_3$)$_2$NCH$_2$CH(—O)CH$_2$N(CH$_3$)$_2$)O—), 9.21 to 8.92 multiple peaks, —OSi(CH$_3$)$_3$).

Example 5

Cyclotetra(3-amino-1-propoxy)methylsiloxane

Cyclotetra(3-amino-1-propoxy)methylsiloxane was synthesized according to the method described in Example 2 except that cyclotetra(methylhydro)siloxane (7) (1.21 ml, 0.02 mol) was used in place of 1,3-bis(trimethylsiloxy)-1,3-dimethylsiloxane and 3-amino-1-propanol was used as the amino alcohol. Method B was used to isolate the product in 94% yield.

The $^1$H NMR spectra for the product were as follows: $^1$H δ=0.17 (bs, 3H, —OSi(CH$_3$)(OCH$_2$CH$_2$CH$_2$NH$_2$)O—), 0.80 (bs, 2H, —OCH$_2$CH$_2$CH$_2$NH$_2$), 1.65 (bs, 2H, —OCH$_2$CH$_2$CH$_2$NH$_2$), 2.75 (bs, 2H, —OCH$_2$CH$_2$CH$_2$NH$_2$), 3.91 (bs, 2H, —OCH$_2$CH$_2$CH$_2$NH$_2$).

The $^{13}$C NMR spectra for the product were as follows: $^{13}$C δ=−3.00 to −7.00 (multiple peaks, —OSi(CH$_3$)(OCH$_2$CH$_2$CH$_2$NH$_2$)O—), 36.94 (—OCH$_2$CH$_2$CH$_2$NH$_2$), 39.51 (—OCH$_2$CH$_2$CH$_2$NH$_2$), 60.87 (—OCH$_2$CH$_2$CH$_2$NH$_2$).

The $^{29}$Si NMR spectra for the product were as follows: $^{29}$Si δ=−57.4 to −59.5 (multiple peaks, —OSi(CH$_3$)(OCH$_2$CH$_2$CH$_2$NH$_2$)O—).

FT-Infrared spectra for the product were as follows: IR in C$_6$D$_6$: —NH$_2$ absorbances at 3391 cm$^{-1}$ and 3310 cm$^{-1}$.

Example 6

Cyclotetra(1,3-(N,N-dimethylamino)-2-propoxy)methylsiloxane

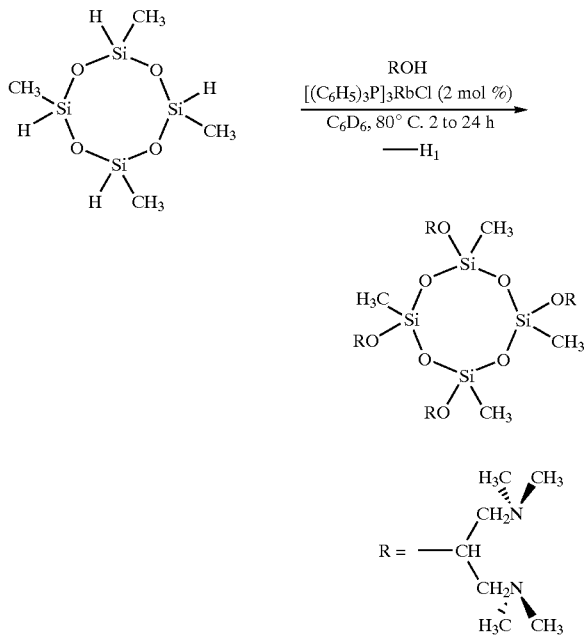

Cyclotetra(1,3-(N,N-dimethylamino)-2-propoxy)methylsiloxane was prepared according to the method described in Example 2, except that cyclotetra(methylhydro)siloxane (1.21 ml, 0.02 mol) was used in place of 1,3-bis(trimethylsiloxy)-1,3-dimethylsiloxane, and 1,3-(N,N-dimethylamino)-2-propanol (3.26 ml, 0.02 mol) was used as the amino alcohol. Method B was used to isolate the product in 98% yield.

The $^1$H NMR spectra for the product were as follows: $^1$H δ=0.42 (s, 6H, —OSi(CH$_3$)((CH$_3$)$_2$NCH$_2$CH(—O)CH$_2$N(CH$_3$)$_2$)O—), 2.22 (s, 12H, (CH$_3$)$_2$NCH$_2$CH(—O)CH$_2$N(CH$_3$)$_2$), 2.47 (dm, 4H, (CH$_3$)$_2$NCH$_2$CH(—O)CH$_2$N(CH$_3$)$_2$), 4.22 (p, 1H, (CH$_3$)$_2$NCH$_2$CH(—O)CH$_2$N(CH$_3$)$_2$).

The $^{13}$C NMR spectra for the product were as follows: $^{13}$C δ=−2.37 (—OSi(CH$_3$)(CH$_3$)$_2$NCH$_2$CH(—O)CH$_2$N(CH$_{13}$)$_2$)O—), 46.98 (CH$_3$)$_2$NCH$_2$CH(—O)CH$_2$N(CH$_3$)$_2$), 64.92 (CH$_3$)$_2$NCH$_2$CH(—O)CH$_2$N(CH$_3$)$_2$), 70.65 (CH$_3$)$_2$NCH$_2$CH(—O)CH$_2$N(CH$_3$)$_2$).

The $^{29}$Si NMR spectra for the product were as follows: $^{29}$Si δ=−58.0 to −60.60 (multiple peaks —OSi(CH$_3$)((CH$_3$)$_2$NCH$_2$CH(—O)CH$_2$N(CH$_3$)$_2$)O—).

IX. Examples 7–10

In Examples 7–10, an aminofunctional alkoxy siloxane was formed by reacting a poly(methylhydro)siloxane (PMHS) with the corresponding amino alcohol in the presence of a rhodium catalyst. The reactions were monitored by multinuclear NMR. In a typical experiment, RhCl(PPh$_3$)$_3$ (0.04 mmol) was dissolved in benzene-d$_6$, (0.5 mL) in a NMR tube, followed by the addition of benzyl alcohol (0.216 mL, 2 mmol) and (0.120 mL, 2 mmol). This mixture was degassed by 3–4 freeze pump-thaw cycles and heated in an oil bath at 78 C, just below the refluxing temperature, under a constant flow of argon. During the course of the reaction, evolution of a gas (presumably H$_2$) was observed.

For Examples 7–10, all reactions were carried out under an atmosphere of argon. Air sensitive products and reagents were handled by standard "Schlenk" techniques. All solvents were dried and distilled from purple solutions of sodium/benzophenone or P$_2$O$_5$, and glassware was dried in an oven at 110–120° C. prior to use. Poly(methylhydro)siloxane Me$_3$Si—(O—SiMeH—)$_n$—O—SiMe$_3$ (M$_w$~2000; n=33–35) and RhCl(PPh3)$_3$ (99.99%) were obtained from Sigma Aldrich Chemical Co., Inc. of Milwaukee, Wis. and used as received. Commercially available alcohols were used without any further purification, except benzyl alcohol and 2,5-dimethoxybenzyl alcohol, which were distilled prior to use.

$^{29}$Si, $^{13}$C, $^1$H NMR spectra were recorded on JEOL GSX270 and GSX400 spectrometers commercially available from JEOL USA, Inc. of Peabody, Mass. $^1$H and $^{13}$C chemical shifts were measured against Me$_4$Si using solvent resonances as standard locks. $^{29}$Si chemical shifts were referenced to external Me$_4$Si in the same solvent. Molecular weight of the polymers was determined by a Waters gel permeation chromatograph (GPC), commercially available from Waters Corporation of Milford, Mass. with polystyrene as the standard and THF as the solvent. IR spectra were recorded on a Matheson Instruments 2020 Galaxy Series spectrometer (commercially available from Matheson Instruments) as KBr pellets or solutions in CaF$_2$ cells. Elemental analyses were carried out by Galbraith Laboratories Inc. of Knoxville, Tenn.

The following method was used for EXAMPLES 7–10. In a "Schlenk" tube, RhCl(PPh$_3$)$_3$ (~36 mg, 0.04 mmol) was suspended in dry benzene (0.8 mL), followed by the addition of benzylalcohol (0.22 mL, 2 mmol) and PMHS (0.12 mL, 2 mmol). This mixture was degassed by 3–4 freeze pump-thaw cycles and heated in an oil bath at 78 C, under a constant flow of argon. The red color of the catalyst disappeared within about 15 minutes of heating and the reaction mixture turned yellow and homogeneous. During substantially the entire course of the reaction, evolution of $H_2$ was observed. After 24 hours, the mixture was cooled to room temperature, and passed through a dry silica gel pad and eluted with pentane/benzene (20/80). For gram scale preparations (4–7 gm) of these polymers, longer reaction times (48–72 h) were employed.

EXAMPLE 7

Poly(3-(2-pyridyl)-1-propoxy)methysiloxane)

A poly(3-(2-pyridyl)-1-propoxy)methysiloxane) product was made according to the following scheme by reacting poly(methylhydro)siloxane (n=33–35) with 3-(2-pyridyl)-1-propanol:

The $^{29}$Si NMR spectra for the product were as follows: $^{29}$Si-NMR ($C_6D_6$, 25° C.); −56.63, −56.7 (very small); −57.26; −57.34; −57.41 (SiMe); +9.62 (terminal $OSiMe_3$). Analysis calculated for $C_8H_{10}O_2Si$: C 57.83, H 6.02, Si 16.86; Found: C 57.85, H 6.00, Si 16.88.

The molecular weight ($M_w$) determined by gel permeation chromatography (GPC) was 5600 ($M_w/M_n$=1.19) relative to polystyrene standard, which was found in relative agreement with calculated values ($M_w$~5445–5775 for n=32–35) indicating total substitution of Si—H bonds with backbone preservation. GPC(THF/polystyrene): $M_w$=5600 ($M_w/M_n$=1.19).

In order to access the stability of these polymers towards hydrolysis, the product was dissolved in benzene-$D_6$ and treated with 3-fold excess of $D_2O$. Polymer degradation was monitored by NMR. After 3 hours at RT<10%, conversion

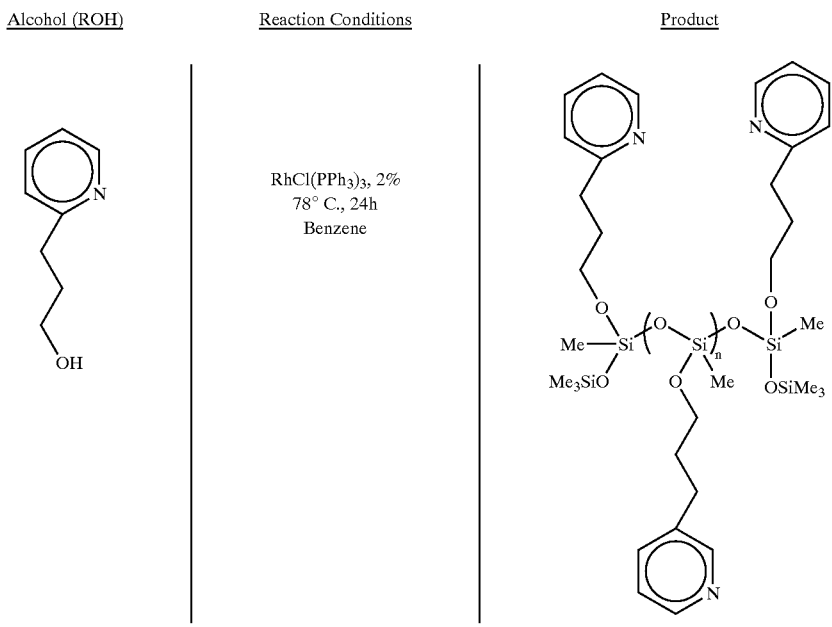

Color changes during the course of the reaction provided an indication of the reaction progress. As the reaction proceeded, the yellow color turned orange and returned to light red after about 24 hours when the reaction was substantially completed. Solvent evaporation under reduced pressure provided the product to be recovered in a yield of 97%.

The $^1$H NMR showed the absence of Si—H signals and Si—$CH_3$/O—$CH_2$Ph resonances in a ratio consistent with the proposed structure. The $^1$H NMR spectra for the product were as follows: $^1$H-NMR ($C_6D_6$, 25° C.); δ 0.13 (s, $OSiMe_3$); 0.30 (s, broad, SiMe); 4.84–4.90 (s, broad, $OCH_2$); 7.14, 7.32 (broad, aromatics).

The $^{13}$C NMR spectra for the product were as follows: $^{13}$C-NMR ($C_6D_6$, 25° C.); δ 1.55 ($OSiMe_3$); −4.12 (broad, SiMe); 64.35 (broad, $OCH_2$); 126.53, 127.14, 128.30, 140.44 (broad, aromatics).

After about 24 hours, the $^{29}$Si spectrum displayed the formation of the product in essentially quantitative yield.

of $SiOCH_2Ph$ bonds to SiOH/SiOSi bonds was observed. After 2.5 hours of heating at 78 C, only 25% of the $SiOCH_2Ph$ bonds were cleaved.

Example 8

Poly(3-(4-pyridyl)-1-propoxy)methysiloxane)

A poly(3-(4-pyridyl)-1-propoxy)methysiloxane) product was made according to the following scheme by reacting poly(methylhydro)siloxane (n=33–35) with 3-(4-pyridyl)-1-propanol:

| Alcohol (ROH) | Reaction Conditions | Product |
|---|---|---|
|  | RhCl(PPh₃)₃, 2%<br>78° C., 24h<br>Benzene | 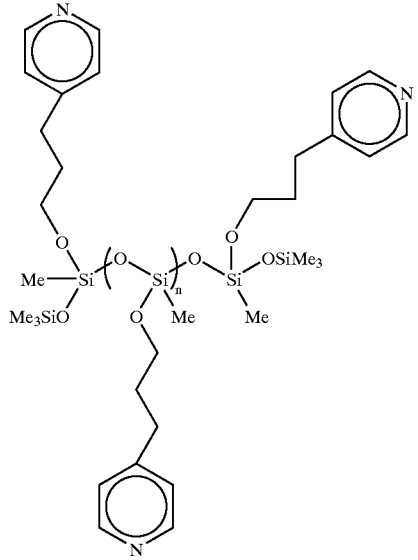 |

The product was recovered in a yield of 93%.

The $^1$H NMR spectra for the product were as follows:
$^1$H-NMR (C$_6$D$_6$, 25° C.); δ 0.14 (s, OSiMe$_3$); 0.34 (s, broad, SiMe); 1.22 (t, broad, CH$_3$); 1.88 (m, broad, CH$_2$); 4.01 (t, broad, OCH$_2$).

The $^{13}$C NMR spectra for the product were as follows:
$^{13}$C-NMR (C$_6$D$_6$, 25° C.); δ 1.42 (OSiMe$_3$); −0.5 (SiMe); 10.60 (CH$_3$); 24.70 (CH$_2$); 62.91 (OCH$_2$)

The $^{29}$Si NMR spectra for the product were as follows:
$^{29}$Si-NMR (C$_6$D$_6$, 25° C.); −57.94 (SiMe); +8.51 (terminal OSiMe$_3$).

Example 9

Poly((N-methyl-4-piperidyloxy)methysiloxane)

A poly((N-methyl-4-piperidyloxy)methysiloxane) product was made according to the following scheme by reacting poly(methylhydro)siloxane (n=33–35) with N-methyl-4-piperidinol:

| Alcohol (ROH) | Reaction Conditions | Product |
|---|---|---|
| 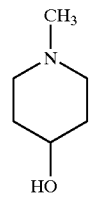 | RhCl(PPh₃)₃, 2%<br>78° C., 48h<br>Benzene | 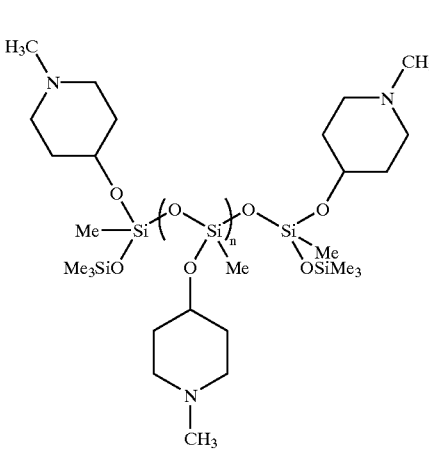 |

The product was recovered in a yield of 95%.

The $^1$H NMR spectra for the product were as follows: $^1$H-NMR (C$_6$D$_6$, 25° C.); δ 0.15 (s, OSiMe$_3$); −0.014 (s, broad, SiMe); 1.11 (d, CH$_3$); 4.12 (q, broad, OCH).

The $^{13}$C NMR spectra for the product were as follows: $^{13}$C-NMR (C$_6$D$_6$, 25° C.); δ 1.72 (OSiMe$_3$); −3.02 (SiMe); 15.69 (CH$_3$); 64.60 (OCH).

The $^{29}$Si NMR spectra for the product were as follows: $^{29}$Si-NMR (C$_6$D$_6$, 25° C.); −60.01 (broad, SiMe); +7.95 (terminal OSiMe$_3$).

Example 10

Poly(4-(N,N-dimethylamino)-phenoxy) methysiloxane)

A poly(4-(N,N-dimethylamino)-phenoxy)methysiloxane) product was made according to the following scheme by reacting poly(methylhydro)siloxane (n=33–35) with 4-(N,N-dimethylamino)-phenol:

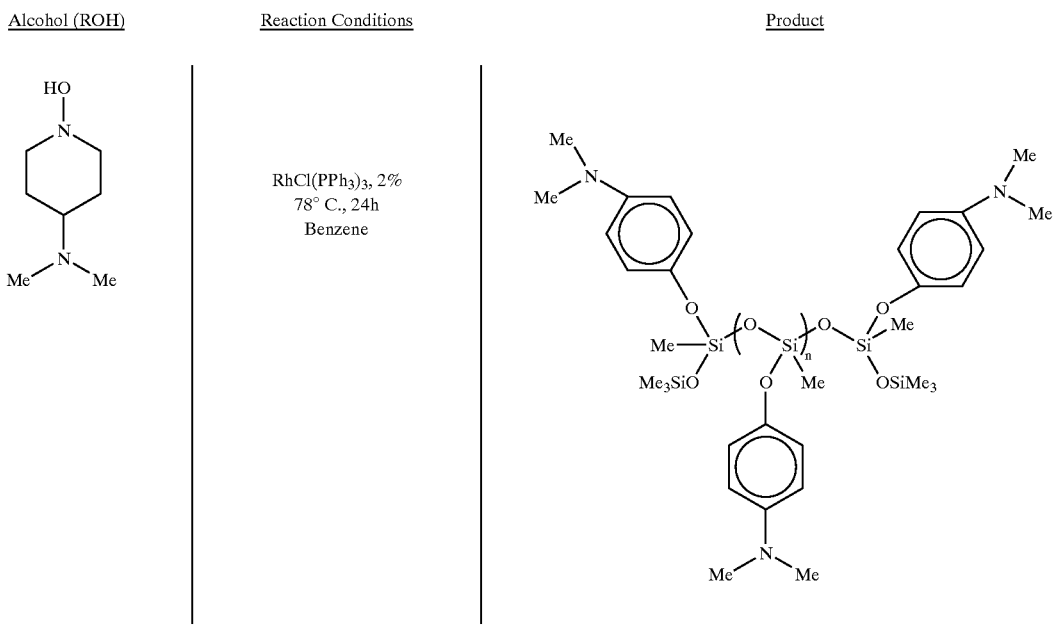

The product was recovered in a yield of 91%.

The $^1$H NMR spectra for the product were as follows: $^1$H-NMR (C$_6$D$_6$, 25° C.); δ 0.13 (s, OSiMe$_3$); 0.32 (s, broad, SiMe); 2.12 (m, broad, CH$_2$); 2.91 (t, broad, CH$_2$); 3.92 (t, broad, OCH$_2$); {6.69 (t, broad), 6.94 (d, broad), 7.18 (m, broad), 8.43 (broad) aromatics}.

The $^{29}$Si NMR spectra for the product were as follows: $^{29}$Si-NMR (C$_6$D$_6$, 25° C.); δ −57.20, −57.95, −58.06, −58.16 (SiMe); +9.08 (terminal OSiMe$_3$). Analysis calculated for C$_9$H$_{13}$O$_2$NSi: C 55.38, H 6.66, N 7.17; Found: C 55.39, H 6.67, N 7.19.

GPC(THF/polystyrene): M$_w$=6538 (M$_w$/M$_n$=1.12).

It is important to note that the construction and arrangement of the elements of the poly((aminofunctional alkoxy)-alkylsiloxane) compounds as shown and described in the various embodiments is illustrative only. Although only a few embodiments of the present inventions have been described in detail in this disclosure, those skilled in the art who review this disclosure will readily appreciate that many modifications are possible without materially departing from the novel teachings and advantages of the subject matter described in this disclosure. Other substitutions, modifications, changes and omissions may be made in the design, operating conditions and arrangement of the exemplary embodiments without departing from the spirit of the present invention.

What is claimed is:

1. A method of producing a polyaminofunctional alkoxy polysiloxane comprising:
    reacting a polyhydrosiloxane with an alcohol reactant in the presence of a dehydrogenative coupling catalyst to form a polyaminofunctional alkoxy polysiloxane;
    wherein the alcohol reactant includes an polyaminofunctional alcohol.

2. The method of claim 1 wherein the dehydrogenative coupling catalyst includes a rhodium compound.

3. The method of claim 2 wherein the dehydrogenative coupling catalyst includes ((C$_6$H$_5$)$_3$P)$_3$RhCl.

4. The method of claim 1 wherein the polyhydrosiloxane is reacted with the polyaminofunctional alcohol in a solvent which includes a hydrocarbon solvent, a halogenated hydrocarbon solvent, an ether or a mixture thereof.

5. The method of claim 1 wherein the polyhydrosiloxane is reacted with the polyaminofunctional alcohol under substantially anhydrous or deoxygenated conditions.

6. The method of claim 1 wherein the polyhydrosiloxane is reacted with the polyaminofunctional alcohol at a temperature of about 0° C. to 200° C.

7. The method of claim 1 comprising reacting a cyclic polyhydrosiloxane with the polyaminofunctional alcohol to form a cyclic polyaminofunctional alkoxy polysiloxane.

8. The method of claim 1 comprising reacting a linear polyhydrosiloxane with the polyaminofunctional alcohol to form a linear polyaminofunctional alkoxy polysiloxane.

9. A method of producing an aminofunctional alkoxy polysiloxane comprising:
    reacting a polyhydrosiloxane with an alcohol reactant in the presence of a dehydrogenative coupling catalyst to form an aminofunctional alkoxy polysiloxane;
    wherein the aminofunctional alkoxy polysiloxane includes an aromatic amino group.

10. The method of producing the aminofunctional alkoxy polysiloxane of claim 9, wherein the aromatic amino group includes a pyridyl group, a pyrimidyl group or a pyrazinyl group.

11. The method of claim 9 comprising reacting a cyclic polyhydrosiloxane with the aminofunctional alcohol to form a cyclic aminofunctional alkoxy polysiloxane.

12. The method of claim 9 comprising reacting a linear polyhydrosiloxane with the aminofunctional alcohol to form a linear aminofunctional alkoxy polysiloxane.

13. The method of claim 9 wherein the dehydrogenative coupling catalyst includes a rhodium compound.

14. A linear polyaminofunctional alkoxy polysiloxane having the formula:

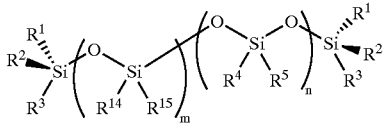

wherein n is an integer from 2 to 1,000 and m is an integer from 0 to 1,000;

$R^1$, $R^2$ and $R^3$ are independently $C_1$–$C_{10}$ alkyl, cyclopentyl, cyclohexyl, benzyl, toluyl, xylyl or phenyl;

$R^4$ is hydrogen, $C_1$–$C_{10}$ alkyl, cyclopentyl, cyclohexyl, benzyl, toluyl, xylyl, phenyl or an alkoxy group;

$R^5$ is a polyaminofunctional alkoxy group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl, or an alkoxy group.

15. The polysiloxane of claim 14 wherein $R^1$, $R^2$ and $R^3$ are independently lower alkyl.

16. The polysiloxane of claim 14 wherein $R^4$ is methyl.

17. The polysiloxane of claim 14 wherein the polyaminofunctional alkoxy group includes an aliphatic amino group.

18. The polysiloxane of claim 14 wherein the polyaminofunctional alkoxy group includes a cycloaliphatic amino group.

19. The polysiloxane of claim 14 wherein the polyaminofunctional alkoxy group includes a primary amino group.

20. The polysiloxane of claim 14 wherein the polyaminofunctional alkoxy group includes a secondary amino group.

21. The polysiloxane of claim 14 wherein the polyaminofunctional alkoxy group includes a tertiary amino group.

22. The polysiloxane of claim 14 wherein the polyaminofunctional alkoxy group includes an aminophenyl group.

23. The polysiloxane of claim 14 wherein the polyaminofunctional alkoxy group includes a piperidinyl group.

24. The polysiloxane of claim 14 wherein the polyaminofunctional alkoxy group includes a piperazinyl group.

25. The polysiloxane of claim 14 wherein the polyaminofunctional alkoxy group includes a pyrrolidinyl group.

26. The polysiloxane of claim 14 wherein n is an integer of 2 and m is an integer of 0.

27. A linear aminofunctional alkoxy polysiloxane having the formula:

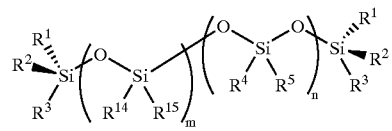

wherein n is an integer from 2 to 1,000 and m is an integer from 0 to 1,000;

$R^1$, $R^2$ and $R^3$ are independently $C_1$–$C_{10}$ alkyl, cyclopentyl, cyclohexyl, benzyl, toluyl, xylyl or phenyl;

$R^4$ is hydrogen, $C_1$–$C_{10}$ alkyl, cyclopentyl, cyclohexyl, benzyl, toluyl, xylyl, phenyl or an alkoxy group;

$R^5$ is an aminofunctional alkoxy group that includes an aromatic amino group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl, or an alkoxy group.

28. The polysiloxane of claim 27 wherein the aromatic amino group includes a pyridyl group.

29. The polysiloxane of claim 27 wherein the aromatic amino group includes a pyrimidyl group.

30. The polysiloxane of claim 27 wherein the aromatic amino group includes a pyrazinyl group.

31. The polysiloxane of claim 27 wherein n is an integer of 2 and m is an integer of 0.

32. A cyclic polyaminofunctional alkoxy polysiloxane having the formula:

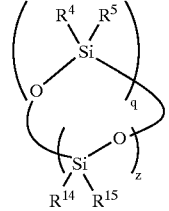

wherein q is an integer from 1 to 12; z is an integer from 0 to 11; and q+z=an integer from 3 to 12;

$R^4$ is hydrogen, $C_1$–$C_{10}$ alkyl, cyclopentyl, cyclohexyl, benzyl, toluyl, xylyl, phenyl or an alkoxy group;

$R^5$ is a polyaminofunctional alkoxy group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl or an alkoxy group.

33. The polysiloxane of claim 32 wherein the polyaminofunctional alkoxy group includes an aliphatic amino group.

34. The polysiloxane of claim 32 wherein the polyaminofunctional alkoxy group includes a cycloaliphatic amino group.

35. The polysiloxane of claim 32 wherein the polyaminofunctional alkoxy group includes a primary amino group.

36. The polysiloxane of claim 32 wherein the polyaminofunctional alkoxy group includes a secondary amino group.

37. The polysiloxane of claim 32 wherein the polyaminofunctional alkoxy group includes a tertiary amino group.

38. The polysiloxane of claim 32 wherein the polyaminofunctional alkoxy group includes an aminophenyl group.

39. The polysiloxane of claim 32 wherein the polyaminofunctional alkoxy group includes a piperidinyl group.

40. The polysiloxane of claim 32 wherein the polyaminofunctional alkoxy group includes a piperazinyl group.

41. The polysiloxane of claim 32 wherein the polyaminofunctional alkoxy group includes a pyrrolidinyl group.

42. A cyclic aminofunctional alkoxy polysiloxane having the formula:

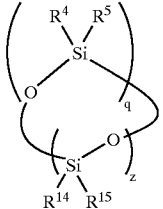

wherein q is an integer from 1 to 12; z is an integer from 0 to 11; and q+z=an integer from 3 to 12;

$R^4$ is hydrogen, $C_1$–$C_{10}$ alkyl, cyclopentyl, cyclohexyl, benzyl, toluyl, xylyl, phenyl or an alkoxy group;

$R^5$ is an aminofunctional alkoxy group that includes an aromatic amino group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl or an alkoxy group.

43. The polysiloxane of claim 42 wherein the aromatic amino group includes a pyridyl group.

44. The polysiloxane of claim 42 wherein the aromatic amino group includes a pyrimidyl group.

45. The polysiloxane of claim 42 wherein the aromatic amino group includes a pyrazinyl group.

46. A coating composition comprising a polyaminofunctional alkoxy polysiloxane.

47. The coating composition of claim 46 wherein the polyaminofunctional alkoxy polysiloxane includes an aliphatic amino group.

48. The coating composition of claim 46 wherein the polyaminofunctional alkoxy polysiloxane includes a cycloaliphatic amino group.

49. The coating composition of claim 46 wherein the polyaminofunctional alkoxy polysiloxane includes a primary amino group.

50. The coating composition of claim 46 wherein the polyaminofunctional alkoxy polysiloxane includes a secondary amino group.

51. The coating composition of claim 46 wherein the polyaminofunctional alkoxy polysiloxane includes a tertiary amino group.

52. The coating composition of claim 46 wherein the polyaminofunctional alkoxy polysiloxane includes an aminophenyl group.

53. The coating composition of claim 46 wherein the polyaminofunctional alkoxy polysiloxane includes a piperidinyl group, a piperazinyl group or a pyrrolidinyl group.

54. The coating composition of claim 46 wherein the polyaminofunctional alkoxy polysiloxane includes a cyclic polyaminofunctional alkoxy polysiloxane.

55. The coating composition of claim 46 wherein the polyaminofunctional alkoxy polysiloxane includes a linear polyaminofunctional alkoxy polysiloxane.

56. The coating composition of claim 46 wherein the polysiloxane includes a compound of the formula:

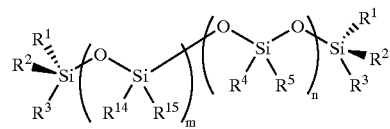

wherein n is an integer from 2 to 1,000 and m is an integer from 0 to 1,000;

$R^1$, $R^2$ and $R^3$ are independently $C_1$–$C_{10}$ alkyl, cyclopentyl, cyclohexyl, benzyl, toluyl, xylyl or phenyl;

$R^4$ is hydrogen, $C_1$–$C_{10}$ alkyl, cyclopentyl, cyclohexyl, benzyl, toluyl, xylyl, phenyl or an alkoxy group;

$R^5$ is a polyaminofunctional alkoxy group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl, or an alkoxy group.

57. A coating composition comprising an aminofunctional alkoxy polysiloxane that includes an aromatic amino group.

58. The coating composition of claim 57 wherein the aromatic amino group includes a pyridyl group.

59. The coating composition of claim 57 wherein the aromatic amino group includes a pyrimidyl group.

60. The coating composition of claim 57 wherein the aromatic amino group includes a pyrazinyl group.

61. The coating composition of claim 57 wherein the aminofunctional alkoxy polysiloxane includes a cyclic aminofunctional alkoxy polysiloxane.

62. The coating composition of claim 57 wherein the aminofunctional alkoxy polysiloxane includes a linear aminofunctional alkoxy polysiloxane.

63. The coating composition of claim 57 wherein the polysiloxane includes a compound of the formula:

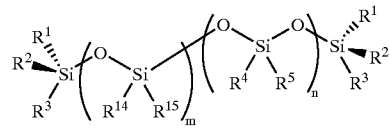

wherein n is an integer from 2 to 1,000 and m is an integer from 0 to 1,000;

$R^1$, $R^2$ and $R^3$ are independently $C_1$–$C_{10}$ alkyl, cyclopentyl, cyclohexyl, benzyl, toluyl, xylyl or phenyl;

$R^4$ is hydrogen, $C_1$–$C_{10}$ alkyl, cyclopentyl, cyclohexyl, benzyl, toluyl, xylyl, phenyl or an alkoxy group;

$R^5$ is an aminofunctional alkoxy group that includes an aromatic amino group;

$R^{14}$ is hydrogen, $C_1$–$C_{10}$ alkyl, cyclopentyl, cyclohexyl, benzyl, toluyl, xylyl, phenyl or an alkoxy group; and $R^{15}$ is hydrogen, $C_1$–$C_{10}$ alkyl, cyclopentyl, cyclohexyl, benzyl, toluyl, xylyl, phenyl, or an alkoxy group.

* * * * *

UNITED STATES PATENT AND TRADEMARK OFFICE
CERTIFICATE OF CORRECTION

PATENT NO.   : 6,482,912 B2
DATED        : November 19, 2002
INVENTOR(S)  : Philip Boudjouk et al.

It is certified that error appears in the above-identified patent and that said Letters Patent is hereby corrected as shown below:

Column 3,
Line 64, equation, second column, below arrow, delete "C.2" and insert -- C,2 --;

Column 7,
Line 48, following "additional", delete "suit" and insert -- suitable --;
Table 1, second line, delete "$((C_8H_{14})_2RhCl_2$" and insert -- $((C_8H_{14})_2RhCl)_2$ --;

Column 8,
Line 13, following metal, delete "secies." and insert -- species. --;

Column 13,
Line 64, preceding "ml", insert -- 5 --;

Column 16,
Example 3, lines 36 and 45, in both instances where "$CH_2$" appears directly above "$CH_3$", delete "$CH_2$" and insert -- $CH_3$ --;
Line 36, delete "$(CH_{2)3})$" and insert -- $(CH_2)_3$ --;

Column 17,
Example 6, above the arrow, delete "$[(C_6H_5)_3P]_3RbCl$ (2 mol %)" and insert -- $[(C_6H_5)_3P]_3RhCl$ (2 mol %) --;

Column 23,
Example 10, first column, delete "Alcohol (ROH)" column in its entirety and substitute the following

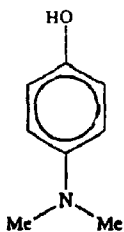

Column 25,
Lines 16-23, delete the formula and insert:

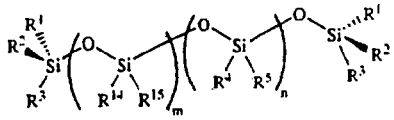

UNITED STATES PATENT AND TRADEMARK OFFICE
CERTIFICATE OF CORRECTION

PATENT NO. : 6,482,912 B2
DATED : November 19, 2002
INVENTOR(S) : Philip Boudjouk et al.

It is certified that error appears in the above-identified patent and that said Letters Patent is hereby corrected as shown below:

Column 26,
Lines 1-8, delete the formula and insert: 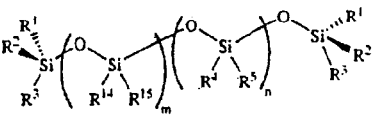

Column 28,
Lines 1-8, delete the formula and insert: 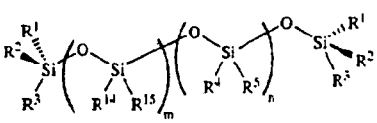

Lines 40-45, delete the formula and insert: 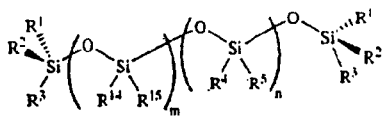

Signed and Sealed this

Eighteenth Day of November, 2003

JAMES E. ROGAN
*Director of the United States Patent and Trademark Office*